(12) United States Patent
Lefevre et al.

(10) Patent No.: US 6,319,470 B1
(45) Date of Patent: Nov. 20, 2001

(54) DEVICE FOR AUTOMATIC PREPARATION OF BLOOD SMEARS ON PLATES

(75) Inventors: Didier Lefevre, Saint Clement de Riviere; Ghislain Morel, Roanne; Henri Champseix, Montferrier sur Lez; Serge Champseix, Tarnac; Roger Le Comte, Perols, all of (FR)

(73) Assignee: ABX, Montpellier Cedex (FR)

( * ) Notice: Subject to any disclaimer, the term of this patent is extended or adjusted under 35 U.S.C. 154(b) by 0 days.

(21) Appl. No.: 09/372,600

(22) Filed: Aug. 12, 1999

(30) Foreign Application Priority Data

Sep. 1, 1998 (FR) .................................................. 98 10910

(51) Int. Cl.$^7$ .............................. G01N 35/10; C12M 1/00
(52) U.S. Cl. .............................. 422/65; 422/67; 422/100; 422/104; 435/286.3
(58) Field of Search ................................. 422/63, 65, 67, 422/100, 104; 436/47, 68.1; 435/286.3; 118/100

(56) References Cited

U.S. PATENT DOCUMENTS

| 4,027,623 | 6/1977 | Adler . |
| 4,034,700 | 7/1977 | Bassett et al. . |
| 5,676,910 | 10/1997 | Levine et al. . |
| 5,766,549 * | 6/1998 | Gao et al. ............................... 422/65 |
| 5,871,696 * | 2/1999 | Roberts et al. ........................ 422/65 |
| 6,110,425 * | 8/2000 | Gao et al. .............................. 422/66 |
| 6,268,208 * | 7/2001 | Kondo .............................. 435/286.3 |

FOREIGN PATENT DOCUMENTS

| 0 323130 | 7/1989 | (EP) . |
| 0 735358 | 10/1996 | (EP) . |
| 0 740142 | 10/1996 | (EP) . |
| 97/26541 | 7/1997 | (WO) . |
| 97/39348 | 10/1997 | (WO) . |

* cited by examiner

*Primary Examiner*—Nina Bhat
(74) *Attorney, Agent, or Firm*—Dennison, Scheiner, Schultz & Wakeman

(57) ABSTRACT

A device for automatic preparation of blood smears on plates comprises a storage unit for stacked new plates, an extractor unit to extract a plate from the stack, a depositing unit. To deposit a drop of blood on a plate, a spreading unit, to spread a drop of blood and produce a blood smear, a marking unit, comprising a marking head which can place means of identification on a reserved area of the plate, a drying unit, which can dry the blood smear, a coloring unit), which can color the blood smear, an output unit to unload the plate, and transfer means, to displace the plate between the aforementioned units, according to a pre-determined path.

13 Claims, 4 Drawing Sheets

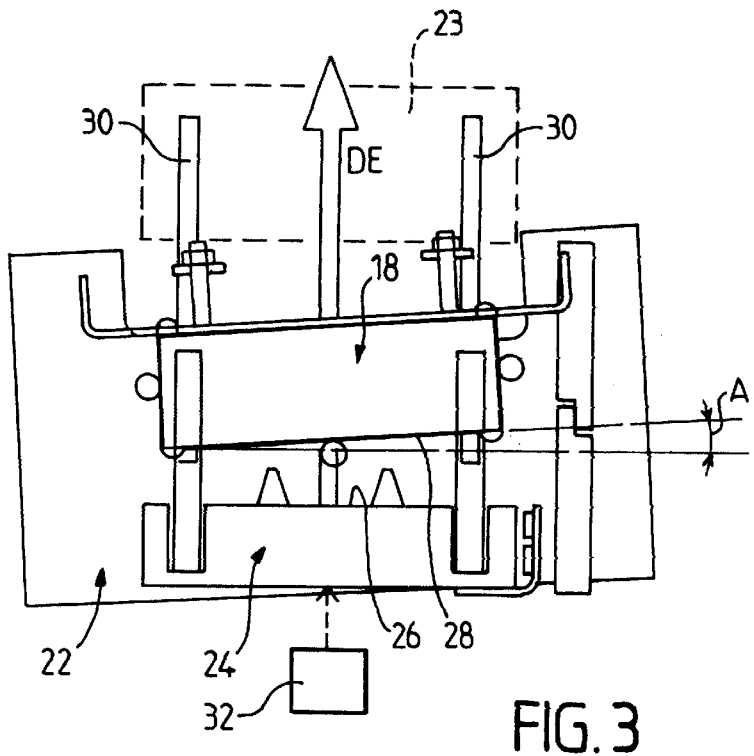
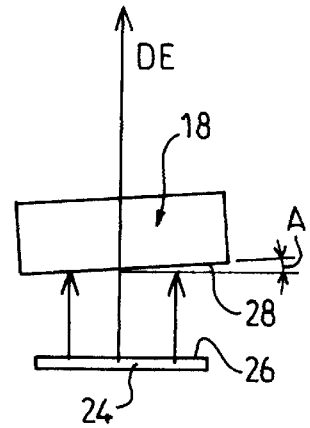
FIG.3　　FIG.4
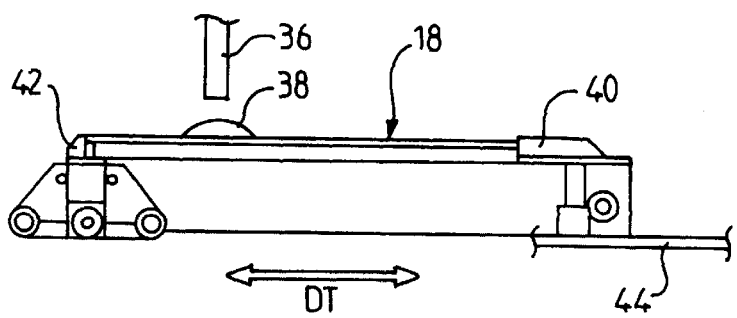
FIG.5
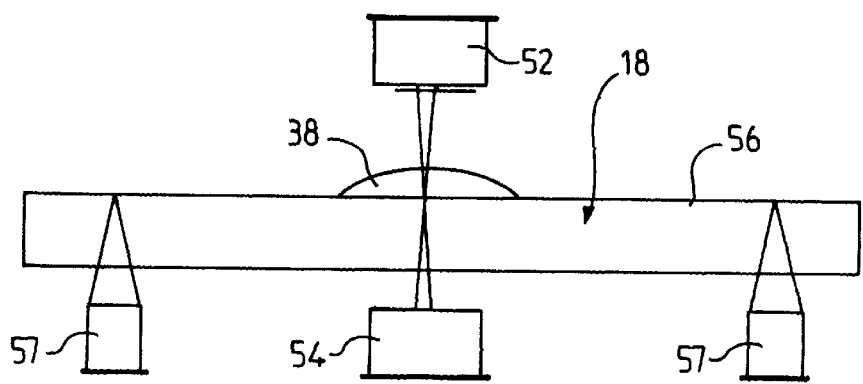
FIG.6

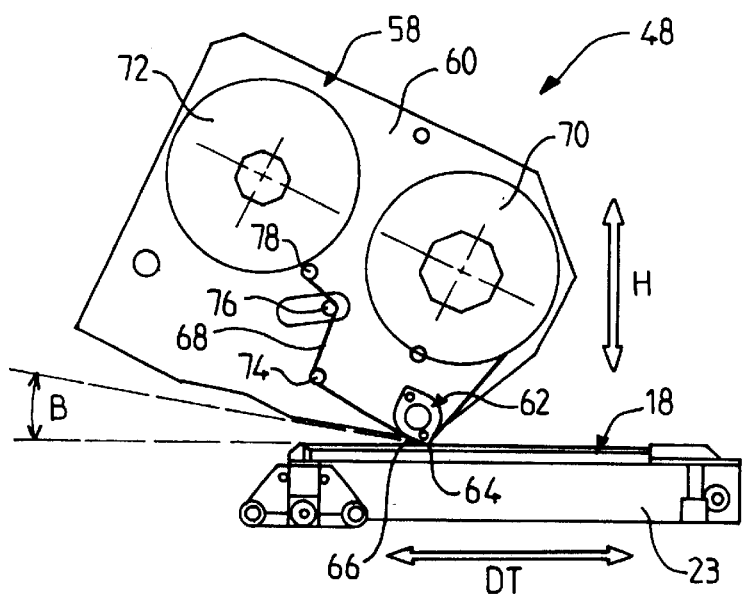
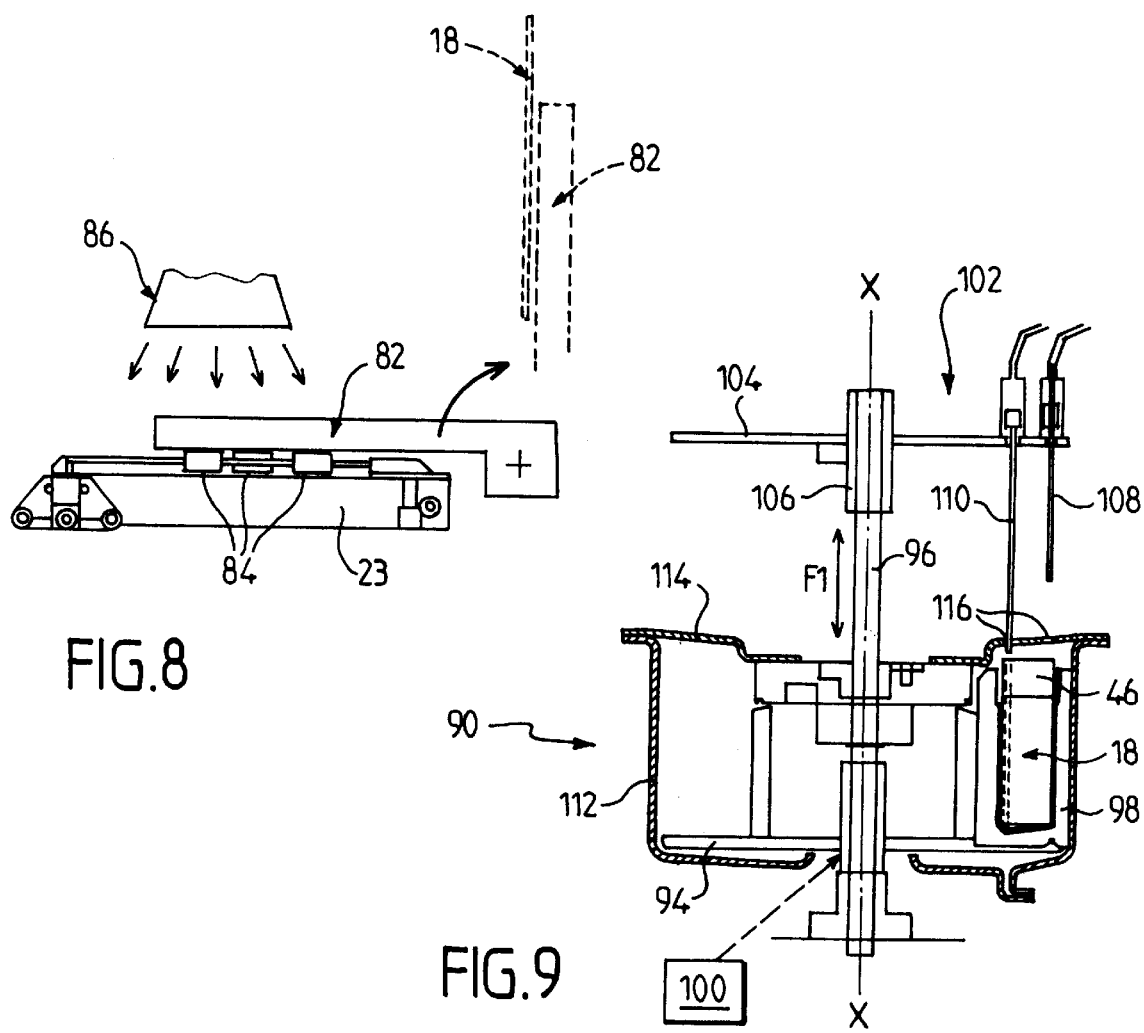

DEVICE FOR AUTOMATIC PREPARATION OF BLOOD SMEARS ON PLATES

BACKGROUND OF THE INVENTION

The invention relates to the field of haematological analyses, and more specifically to the preparation of blood smears on plates.

In this particular field, it is known to deposit a drop of a blood sample on a plate, such as a glass plate for analysis under a microscope, and to spread this drop on the plate in order to produce what is known as a blood smear. The latter is then dried, then coloured by at least one appropriate reagent, in order to permit subsequent analysis under the microscope. In fact, analysis of plates of this type makes it possible to determine the composition of the blood sample concerned, which is of great importance for the diagnosis of specific pathologies.

Blood smears of this type can be prepared by automated devices, which, on the basis of a stock of new plates, carry out a multiplicity of operations of depositing and spreading of blood on plates and miscellaneous subsequent processing operations such as drying and colouring. The plates thus processed are then collected in appropriate containers.

Devices of this type are already known, in particular from publications U.S. Pat. No. 4,034,700, EP 0 735 358, and WO 97/18457.

However, automatic preparation of plates of this type poses various problems, in particular concerning spreading of the blood, which must be perfectly controlled in order to obtain regular distribution of the cells on the plate, irrespective of the quantity of cells present in the blood.

It is also necessary for this spreading to be carried out without any risk of contamination from a previous spreading operation.

Another problem is associated with handling of the plates themselves, which consist of thin, relatively fragile glass plates, which also have the disadvantage that they have a natural tendency to adhere to one another when they are new, and are disposed in stacks.

Yet another problem is associated with the use of toxic products in order to carry out the operations of colouring of the plates, from bottles of reagents, and also with the rinsing operations which are carried out by solvents. It is thus essential to be able to prevent the migration of toxic vapours.

All of these problems, and others, have not yet been solved satisfactorily by the devices for preparation of bloods smears which are known according to the prior art.

SUMMARY OF THE INVENTION

In particular, the object of the invention is to solve the above-described problems.

For this purpose, the invention proposes a device for automatic preparation of blood smears on plates, which comprises:

- a storage unit, which can store new plates disposed horizontally, and superimposed in a vertical stack;
- an extractor unit, which can extract a plate from the stack, and comprises a thruster, which can be displaced in a selected direction of extraction, and can act on the plate which is disposed at the base of the stack, in order to transfer the plate to a depositing unit, the thruster being in the form of a blade, which can act on a longitudinal edge of the plate, such that this edge forms an acute angle relative to the level which is perpendicular to the direction of extraction, the said acute angle advantageously having a value of between 1 and 30°;
- a depositing unit, which can deposit a drop of blood on a plate extracted from the stack;
- a spreading unit, which can spread the drop of blood in controlled conditions, in order to produce a regularly distributed blood smear;
- a marking unit, comprising a marking head which can add means of identification on a reserved area of the plate;
- a drying unit, which can dry the blood smear;
- a colouring unit, which can colour the blood smear;
- an output unit, to unload the plate thus coloured; and
- transfer means, which can displace the plate between the aforementioned units, according to a pre-determined path.

The device according to the invention thus makes it possible to carry out the various operations required, by means of specific units to which the plate is transferred in succession, by the transfer means. At these units, the plate undergoes a particular operation, in perfectly controlled conditions.

In particular, the extractor unit makes it possible to extract a plate from the stacking unit, without the aforementioned problems of adhesion.

In addition, the spreading unit spreads the drop of blood in controlled conditions, which makes it possible to produce a regularly distributed blood smear.

According to a preferred embodiment of the invention, the spreading unit comprises a counter-block which can be applied at a predetermined angle, against the surface of the plate on which the drop of blood has been deposited, and means for imparting relative displacement in translation between the plate and the counter-block, in order to produce a blood smear with controlled thickness, and this counter-block is covered with a flexible strip of plastics material, which is supported by means for winding and unwinding, such that the said strip has a part which is in contact with the blood, which strip is displaced between two successive spreading operations, thus making it possible to avoid any risk of contamination.

These means for winding and unwinding advantageously comprise a first bobbin, from which the new strip is unwound, and a second bobbin, onto which the strip which is soiled by the blood is wound, these bobbins preferably being contained in a case.

The spreading unit advantageously comprises a measuring unit, which can measure the optical transmission of the drop of blood deposited on the plate, in order to deduce a measured value, which can be used in order to adjust the spreading speed, and thus the thickness.

The aforementioned measuring unit advantageously comprises an electro-luminescent diode and a photo-diode, which are disposed on both sides of the plate, when the drop of blood is put into place.

According to a preferred embodiment of the invention, the colouring unit comprises a turntable, which is mounted such as to rotate around a vertical axis, and is provided with a plurality of wells which are distributed around the circumference, and can each receive a plate in a vertical position, means to ensure angular rotation of the turntable sequentially from well to well, and also filling and emptying means, in order to fill a well with a processing fluid, and then empty the contents from it.

These filling and emptying means advantageously comprise at least two plunger needles, which are supported by a support which is displaceable in translation, parallel to the axis of rotation of the turntable, between a high position, in which the needles are extracted from the well, and a low position, in which the needles are plunged into the well.

According to an advantageous characteristic of the invention, in the position in which a plate is received in a well, the means of identification of the plate are disposed in the upper part, such that they are outside the fluid which is contained in the well.

According to another advantageous characteristic of the invention, the colouring unit comprises a closed enclosure, which contains the turntable and the wells.

According to a preferred embodiment of the invention, the output unit comprises storage and displacement means, which can store and advance empty containers, which can receive plates output from the colouring unit.

According to a preferred embodiment of the invention, the transfer means comprise a carriage, which can displace the plates one by one in a horizontal position, from the storage unit as far as the drying unit.

In addition, these transfer means advantageously comprise a tilter, which is disposed in the vicinity of the drying unit, and can bring the plate into a vertical position.

Advantageously, the transfer means additionally comprise a handling bracket, which can displace a plate which is in a vertical position, between the drying unit, the colouring unit and the output unit, the bracket comprising a fixed support, a horizontal beam which can be displaced vertically relative to the fixed support, a slide which can be displaced in translation along the beam, and a controlled gripper, which is supported by the slide, and can grasp a plate and then release it, in order to displace it from one unit to another.

In the following description, which is provided purely by way of example, reference is made to the attached drawings.

BRIEF DESCRIPTION OF THE DRAWINGS

FIG. 3 is a plan view of the storage unit and the extractor unit;

FIG. 4 is an illustration of the method of action of the extractor unit;

FIG. 5 shows a sensor which is part of the depositing unit, depositing a drop of blood on a plate which is supported by a carriage;

FIG. 6 shows an optical transmission measuring unit, which is associated with the spreading unit;

FIG. 7 shows a tool of the spreading unit;

FIG. 8 shows a tilter of the drying and tilting unit;

FIG. 9 is a view in vertical cross-section of the colouring unit;

DETAILED DESCRIPTION OF THE PREFERRED EMBODIMENT

Figure 1:
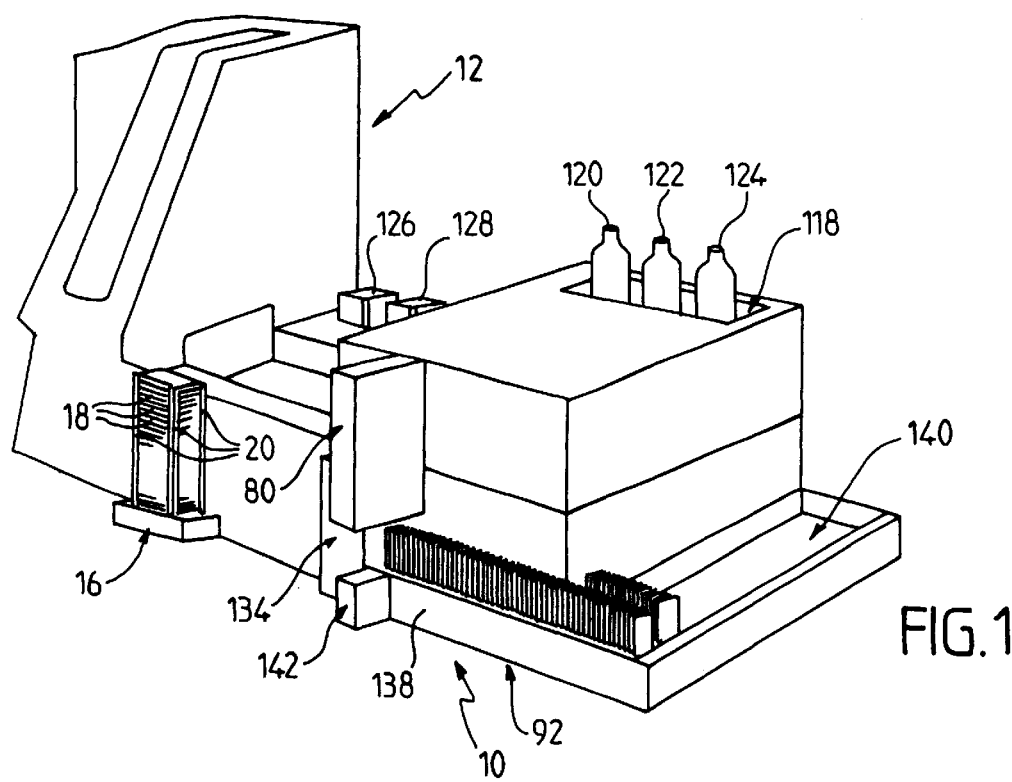
FIG. 1 is a schematic perspective view of a device according to the invention.
Figure 2:
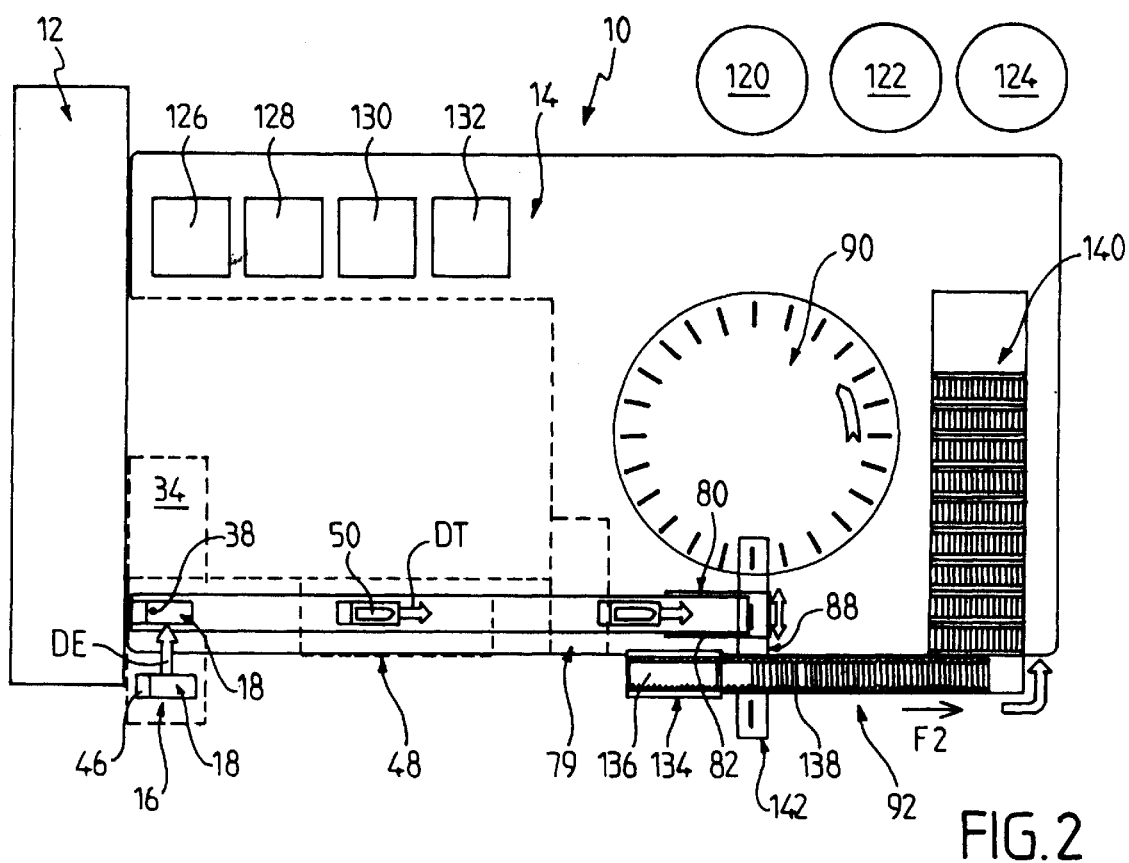
FIG. 2 is a plan view of the device in FIG. 1.

Reference is made firstly to FIGS. 1 and 2, which represent a device 10 for preparation of blood smears according to the invention. In this example, this device is combined with a device 12, which produces haemograms in parallel. In the example, the device 12 is of the ABX VÉGA type, which is sold by the French company ABX.

The device 10 comprises a rectangular base plate 14, which supports various units, and firstly a unit 16 for storage of new plates 18. These plates are rectangular glass plates, which are disposed horizontally, and are superimposed in a vertical stack, and are maintained between columns 20 (FIG. 1). This arrangement permits re-supply during operation, since the operator simply has to place new plates on top of the stack.

The device according to the invention additionally comprises an extractor unit 22 (FIG. 3), which is provided in order to extract the plate which is disposed at the base of the stack, in order to bring it onto a carriage 24 (shown schematically in FIG. 3), which then conveys the plate towards other units contained in the device according to the invention.

Extraction of a plate is always problematic, since the plates tend to adhere to one another, which often gives rise to many stoppages in the automatic devices according to the prior art.

In order to eliminate this problem, according to the invention the extractor unit 22 comprises a thruster 24, which can be displaced in a direction of extraction DE, as shown by an arrow in FIGS. 2, 3 and 4. The thruster 24 is in the form of a horizontal blade, the thickness of which is smaller than that of the plate to be extracted. This blade comprises a longitudinal edge 26, which is also known as a front edge, which can act on a longitudinal edge 28 of the blade 18. A characteristic of the invention is constituted by the fact that the direction of extraction DE is not perpendicular to the edge 28 of the plate. In fact, as can be seen in FIGS. 3 and 4, the longitudinal edge 28 forms an acute angle A relative to the level N which is perpendicular to the direction of extraction DE. The value of the angle A is advantageously between 1 and 30°. In the example, this angle is 3°, such that the longitudinal edge 28 of the plate forms an angle of 93° relative to the direction of extraction DE.

It has been found that the fact of installing the stack of plates with angular offsetting of this type, permits more efficient detachment of the plates, and limits blockages or slowing down caused by plates adhering together. A test has made it possible to show that the average power necessary in order to detach two plates by traction at 90° is approximately 15 Newtons, whereas traction at 93° requires only 5 Newtons.

The thruster 24 is guided in translation by rods 30 (FIG. 3), and its displacement is advantageously obtained by an assembly 32, shown schematically in FIG. 3, which comprises a step motor and a ballscrew.

Once the plate has been placed on the carriage 23, it is at the level of the following unit of the installation, i.e. the depositing unit 34 (FIG. 2). At the unit 34, there is provided a sensor 36 (see FIG. 5) which, in the example, is part of the device 12, but which, as a variant, can be part of the device 10 itself. This sensor is moved by displacement means (not shown), and is designed to collect blood from a sample tube (not shown), and then to deposit a drop of blood 38 (FIGS. 2 and 5) on the new plate 18 which has just been deposited on the carriage 23. On the carriage 23, the plate 18 is maintained between a fixed stop 40 and a tilting gripper 42, which is also known as a clip.

The drop of blood is deposited by means of the sensor 36, in a pre-determined position on the plate, which is kept secured, the carriage 23 being immobilised in translation. The volume of the drop of blood is pre-determined, and can be adjusted by the user.

The carriage 23 can be displaced in horizontal translation, according to a direction of translation DT (FIGS. 2 and 5) which is perpendicular to the direction of extraction DE. The displacement in translation of the carriage is carried out by appropriate drive means, for example by a belt 44, which is shown schematically in FIG. 5.

As can be seen in FIG. 2, the plate 18 has a reserved area 46 with a generally rectangular shape, which is provided at one end of the plate 18, and the drop of blood 38 is deposited on the plate, in the vicinity of this reserved area.

The drive means then displace the carriage 23 towards a unit 48, which is known as the spreading unit (FIG. 2), and is provided in order to spread the drop of blood, and thus form a smear 50. The spreading unit 48 is disposed on the path of the carriage 23 which provides transfer of the plate.

The spreading unit 48 (FIG. 6) comprises a measuring unit which can measure the optical transmission of the drop of blood 38 deposited on the plate. This measuring unit comprises an electro-luminescent diode 52 and a photo-diode 54, which are disposed on both sides of the plate 18, in the position of the drop of blood 38. In this case, the electro-luminescent diode 52 is disposed on the same side as the upper surface 56 of the plate, which receives the drop of blood. In the example, the electro-luminescent diode emits at 560 nm.

There is then deduced a measured value of the optical transmission (TO), which depends on the thickness of the drop and its content. It has been shown by tests that this measurement is inversely proportional to the haematocrit reading of the blood concerned. On the basis of the measurement thus obtained, the spreading speed of the blood, and thus the thickness of the smear, is adjusted.

Thus, a blood sample which contains many cells, and therefore has a high haematocrit reading, provides a lower TO measurement, thus generating a high spreading speed. Conversely, a sample which has a low haematocrit reading provides a high TO measurement, and a low spreading speed.

On the basis of this measurement, it is thus possible to control the spreading speed accurately, and to obtain regular distribution of the cells on the plate, irrespective of the quantity of cells present in the blood sample.

When this measurement has been carried out, the spreading is carried out at the spreading unit 48 by a tool 58, which is represented in FIG. 7. The tool 58 comprises a fixed support 60, which supports a counter-block 62, which is designed to carry out the spreading by relative displacement between the counter-block 62 and the plate 18, which is supported by the carriage 23. In the example, it is the displacement of the plate 18 by the carriage 23, in the direction of translation DT, which gives rise to the spreading. The counter-block 62 remains in a fixed position, except that the height of the support 60 can be regulated as shown by the arrow H. In addition, as can be seen, the counter-block 62 has a ridge 64 which is connected to an edge 66, which forms an adjustable angle B with the upper surface 56 of the plate. This adjustable angle B can be modified as required, in order to adjust the thickness of the smear. In general, the angle B is approximately 30°.

As can be seen in FIG. 7, the counter-block 62 does not come directly into contact with the drop of blood. For this purpose, the invention comprises a flexible strip 68 made of plastics material, for example of polyethylene, which is stretched around the counter-block 62 such as to cover completely the ridge 64 and the edge 66 of the counter-block. The tool 60 comprises means for winding and unwinding the strip 68. These means comprise a first bobbin 70 (unwinding bobbin), from which the new strip is unwound, and a second bobbin 72 (winding bobbin), onto which the strip which is soiled by the blood is wound. Between its passage around the counter-block and winding around the bobbin 72, the strip passes around return rollers 74, 76 and 78.

The part of the strip which is in contact with the blood is displaced between two successive spreading operations, such as to provide a blank portion of strip for the following smear, and thus to prevent any risk of contamination.

Advantageously, the bobbins 70 and 72 are contained in a case, which must be changed when the strip is completely used up.

The plate 18 which supports the smear 50 is then transferred, again by the carriage 23, to a marking unit 79 (FIG. 2), which comprises a marking head, which for example can consist of a print head of the needle matrix type, with an ink ribbon. The plate is marked on the reserve area 46 previously described. This area must be ground or pre-painted, in order to allow the printing inks to adhere well.

It should be noted that in a variant embodiment, the marking can be carried out in another manner, for example by means of a ribbon or other printing means disposed in the position of the spreading unit previously described.

When the marking has been carried out, the carriage 23 transfers the plate 18 to a unit 80, which is a drying and tilting unit (FIGS. 1 and 8). The carriage deposits the plate at the unit 80, and the latter is received by a tilter 82, which allows the empty carriage to return to the depositing unit in order to receive a subsequent plate.

The plate is supported by the tilter 82, by means of rollers 84, of which there are advantageously three, and which are made of polymer. The plate is then subjected to a flow of warm air, maintained at about 40° C, which is conveyed by a forced air heater 86. The tilter 82 (FIGS. 2 and 8) then tilts the plate by 90°, in order to bring it into a vertical position (shown in broken outline in FIG. 8), in which the reserved area 46 of the plate is disposed at the top.

The plate thus brought into a vertical position can then be collected by a handling bracket 88 (FIG. 2), which is described in detail hereinafter with reference to FIGS. 10 and 11. In particular, this bracket makes it possible to transfer the plate to a colouring unit 90, and then to an output unit 92.

The colouring unit 90 (FIG. 9) comprises a turntable 94, which is mounted such as to rotate around a shaft 96 with a vertical axis XX. This turntable supports a plurality of receptacles 98 known as "wells", which are distributed circumferentially, and of which there are thirty two in the example shown. These wells are disposed vertically, and have dimensions which are adapted to those of the plates. The turntable 94 is connected to drive means 100, which are shown schematically in FIG. 9, and can rotate the turntable in successive increments, such as to bring the wells in sequence into different positions. Thus, the turntable can carry out angular rotation sequentially from well to well, for example every 30 seconds. Initially, an empty well is disposed at right-angles to the bracket 88, in order to receive a plate.

The plate then undergoes at least one operation in each sequential position of the turntable.

For this purpose, the colouring unit additionally comprises filling and emptying means 102, which comprise a support 104, which can be displaced in vertical translation parallel to the axis of rotation of the turntable. In the example, the support 104 comprises a drum 106, which can slide along the shaft 96, as shown by the arrow F1. The support 104 supports two plunger needles, which are disposed vertically, i.e. an injection needle 108 and an emptying needle 110. The support 104 can be displaced between a high position, in which the needles are extracted from the well 98 (as shown as a solid line in FIG. 9), and a low position in which the needles are plunged into the well. The position of the needles determines the incubation time, such that the needles are displaced in accordance with the colouring conventions selected.

As can be seen in FIG. 9, in the position in which the plate 18 is accommodated in the well 98, the reserved area 46 of the plate, which bears the means of identification, is disposed at the top, such that it is outside the fluid which is contained in the well.

The colouring unit additionally comprises a closed enclosure, comprising a base 112 and a cover 114, which surrounds completely the turntable 94 and the wells 98 which it contains, such as to prevent migration of toxic vapours derived from the reagents or solvents which are injected into the well. The cover 114 contains holes 116, in order to permit passage of the needles.

The plates which are installed in the wells are immersed in succession in dyes and other treatment fluids, in order to carry out one of the colouring operations necessary in order to identify a plate, according to the known methods of MAY-GRUNWALD, GIEMSA, WRIGHT & WRIGHT GIEMSA.

The device 10 comprises a recess 118 (FIG. 1) in order to accommodate bottles containing various fluids which can be injected into the wells, then emptied.

In the example, a bottle 120 is provided in order to contain a solvent (in this case methanol), as well as two bottles 122 and 124 to contain respectively two different dyes.

It should be noted that the device 12, with which the device 10 according to the invention is combined, comprises recesses to accommodate other reagents 126, 128, 130 and 132 (FIG. 2).

After a complete rotation, the plate, which has thus been processed, returns to its original position, i.e. once more at right-angles relative to the bracket 88.

The output unit comprises a receptacle 134 (FIGS. 1 and 2) which can accommodate empty stacked baskets 136. These baskets are then displaced one by one in a passage 138 in the direction of the arrow F2 (FIGS. 1 and 2). In the example, each of the baskets contains twenty recesses, which can each accommodate a plate in a vertical position, which has been supplied by the handling bracket. A mechanical feed device (not shown) makes it possible to feed the baskets in successive increments, in order to position each recess of a basket in succession beneath the handling bracket, and on each occasion to receive a pretreated plate. When the baskets have been filled, they are stored in a storage area 140, before being retrieved by the operator.

In addition, the device 10 comprises a receptacle 142 for storage of plates which are spread manually, and need to be coloured. In fact, in some cases, it is necessary to colour plates which are already provided with blood which has been smeared manually. This receptacle 142 is also disposed at right-angles relative to the bracket, which thus makes it possible to collect a plate from the receptacle 142, in order to bring it directly to the colouring turntable. When the plate has been coloured, it is displaced, and brought into a basket.

Figure 10:
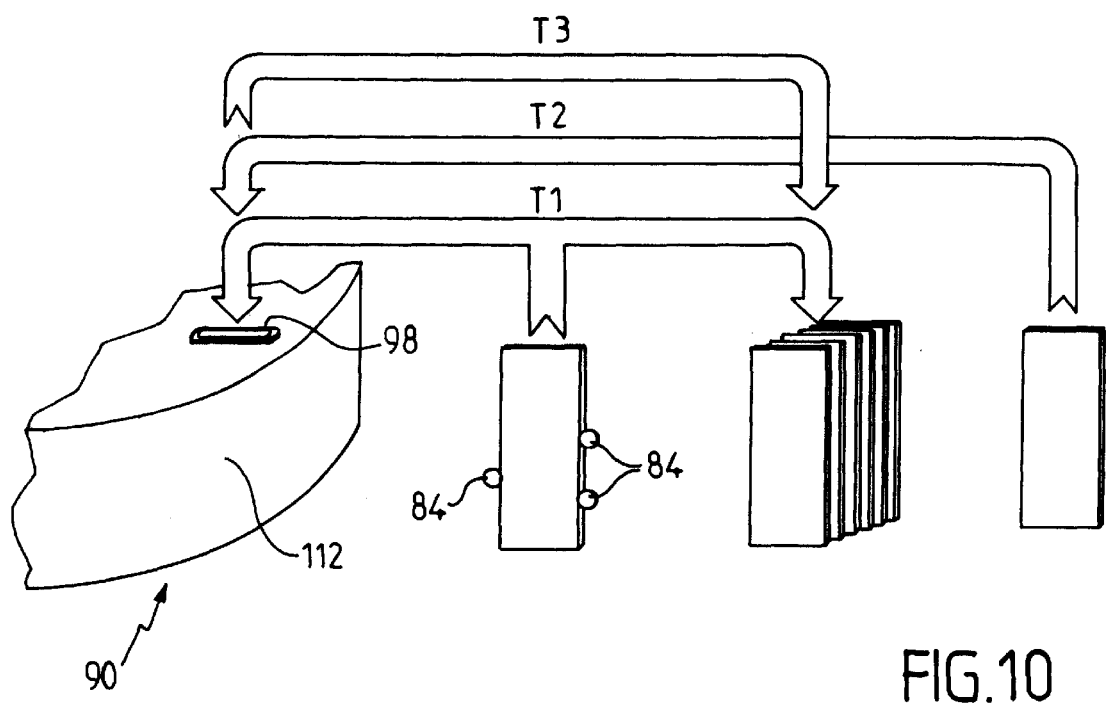
FIG. 10 shows schematically the various paths of the handling bracket.

FIG. 10 shows schematically the various possibilities which are provided by the handling bracket, i.e.: path T1, in order to bring a plate which is provided with a smear to the colouring turntable, or to a basket in the storage area, depending on whether or not colouring is required for this plate. It also makes it possible to travel a path T2, in order, as previously described, to bring a plate which has been spread outside the receptacle 142, to the colouring platform, and a path T3, in order to displace a plate from the colouring platform, to a basket in the storage area.

Figure 11:
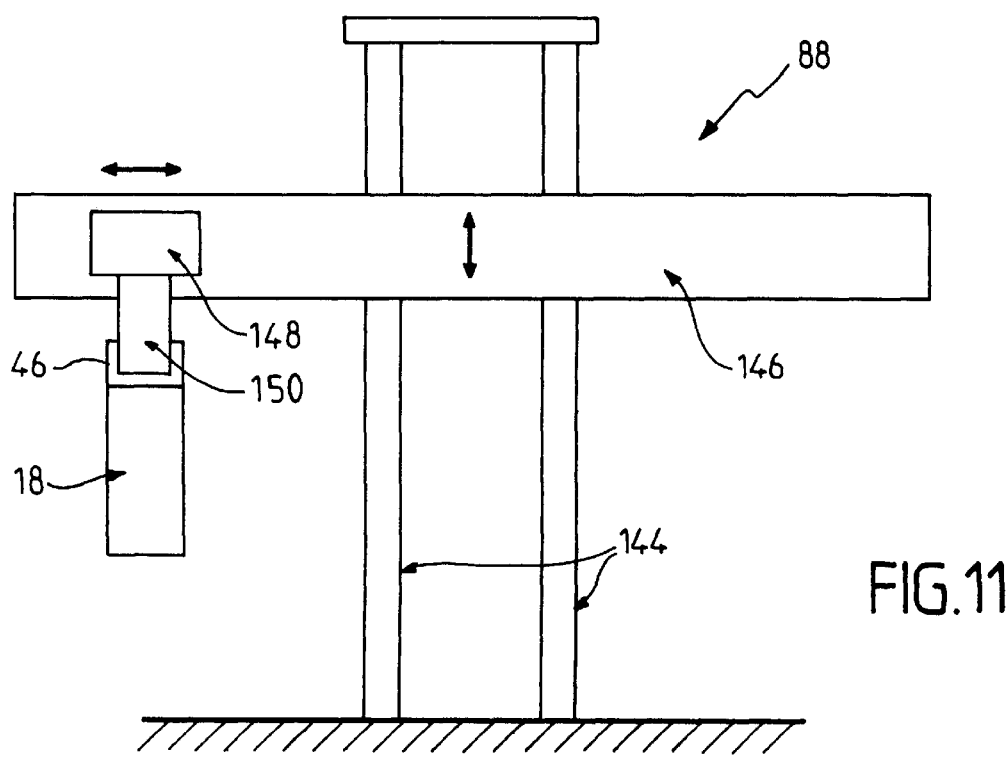
FIG. 11 is a schematic elevated view of the handling bracket.

Reference is now made to FIG. 11, in order to describe the general structure of the bracket 88. The latter comprises a fixed support 144, which consists of two vertical columns which form guide means, a horizontal beam 146, which can be displaced vertically relative to the fixed support, a slide 148, which can be displaced in translation along the beam, and a controlled gripper 150, which can grasp a plate and then release it, in order to displace it from one unit to another.

Appropriate drive means (not shown) make it possible to displace the beam 146 and the slide 148, such that the gripper 150 can occupy different positions in a vertical plane. The gripper 150 can be actuated by any appropriate means, for example by an electro-magnet. It should be noted that the gripper acts on the reserved area 46 of the plate.

Thus, the device according to the invention makes it possible to produce blood smears in automatic conditions, with maximum safety.

What is claimed is:

1. A device for automatic preparation of blood smears on plates, comprising:

a storage unit, to store new plates disposed horizontally, and superimposed in a vertical stack;

a extractor unit, which can extract a plate from the stack, and comprises a thruster, which can be displaced in a selected direction of extraction, and can act on the plate which is disposed at the base of the stack, in order to transfer the plate to a depositing unit, the thruster being in the form of a blade, which can act on a longitudinal edge of the plate, such that this edge forms an acute angle relative to the level which is perpendicular to the direction of extraction, the said acute angle advantageously having a value of between 1 and 30°;

a depositing unit, which can deposit a drop of blood on a plate extracted from the stack;

a spreading unit, which can spread the drop of blood in controlled conditions, in order to produce a regularly distributed blood smear;

a marking unit, comprising a marking head which can add means of identification on a reserved area of the plate;

a drying unit, which can dry the blood smear;

a colouring unit, which can colour the blood smear;

an output unit, to unload the plate thus coloured; and transfer means, which can displace the plate between the aforementioned units, according to a pre-determined path.

2. The device of claim 1, wherein the spreading unit comprises a counter-block which can be applied against the surface of the plate on which the drop of blood has been deposited, forming a pre-determined angle, and means for imparting relative displacement in translation between the plate and the counter-block, in order to produce a blood smear with controlled thickness, and wherein the counter-block is covered with a flexible strip of plastics material, which is supported by means for winding and unwinding, such that the strip has a part which is in contact with the blood, which strip is displaced between two successive spreading operations.

3. The device of claim 2, wherein the means for winding and unwinding advantageously comprise a first bobbin, from which the new strip is unwound, and a second bobbin, onto which the strip which is soiled by the blood is wound, these bobbins preferably being contained in a case.

4. The device of claim 1, wherein the spreading unit comprises a measuring unit, which can measure the optical transmission of the drop of blood deposited on the plate, in order to deduce a measured value, which can be used in order to adjust the spreading speed, and thus the thickness.

5. The device of claim 4, wherein the measuring unit comprises an electro-luminescent diode and a photo-diode, which are disposed on both sides of the plate, when the drop of blood is put into place.

6. The device of claim 1, wherein the colouring unit comprises a turntable, which is mounted such as to rotate around a vertical axis, and is provided with a plurality of wells which are distributed around the circumference, and can each receive a plate in a vertical position, means to ensure angular rotation of the turntable sequentially from well to well, and also filling and emptying means, in order to fill a well with a processing fluid, and then empty the contents from it.

7. The device of claim 6, wherein the filling and emptying means comprise at least two plunger needles, which are supported by a support which is displaceable in translation, parallel to the axis of rotation of the turntable, between a high position, in which the needles are extracted from the well, and a low position, in which the needles are plunged into the well.

8. The device of claim 6, wherein, in the position in which a plate is received in a well, the means of identification of the plate are disposed in the upper part, such that they are outside the fluid which is contained in the well.

9. The device of claim 6, wherein the colouring unit comprises a closed enclosure, which contains the turntable and the wells.

10. The device of claim 1, wherein the output unit comprises storage and displacement means, which can store and advance empty baskets, which can receive plates output from the colouring unit.

11. The device of claim 1, wherein the transfer means comprise a carriage, which can displace the plates one by one in a horizontal position, from the storage unit as far as the drying unit.

12. The device of claim 11, wherein the transfer means additionally comprise a tilter, which is disposed in the vicinity of the drying unit, and can bring the plate into a vertical position.

13. The device of claim 11, wherein the transfer means additionally comprise a handling bracket, which can displace a plate which is in a vertical position, between the drying unit, the colouring unit and the output unit, the bracket comprising a fixed support, a horizontal beam which can be displaced vertically relative to the fixed support, a slide which can be displaced in translation along the beam, and a controlled gripper, which can grasp a plate and release it, in order to displace it from one unit to another.

* * * * *